United States Patent
Park et al.

(10) Patent No.: US 8,670,835 B2
(45) Date of Patent: *Mar. 11, 2014

(54) SYSTEMS AND METHODS FOR COMMUNICATING WITH AN IMPLANTABLE STIMULATOR

(75) Inventors: Rudolph V. Park, Olney, MD (US);
Jordi Parramon, Valencia, CA (US);
Daniel Klosterman, Valencia, CA (US);
Goran N. Marnfeldt, Hollviken (SE)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 163 days.

This patent is subject to a terminal disclaimer.

(21) Appl. No.: 12/789,716

(22) Filed: May 28, 2010
(Under 37 CFR 1.47)

(65) Prior Publication Data

US 2010/0249886 A1 Sep. 30, 2010

Related U.S. Application Data

(63) Continuation of application No. 11/043,404, filed on Jan. 25, 2005, now Pat. No. 7,822,480, which is a continuation-in-part of application No. 10/607,962, filed on Jun. 27, 2003, now Pat. No. 7,177,698.

(60) Provisional application No. 60/392,475, filed on Jun. 28, 2002.

(51) Int. Cl.
*A61N 1/00* (2006.01)

(52) U.S. Cl.
USPC .............................. 607/60; 607/61

(58) Field of Classification Search
None
See application file for complete search history.

(56) References Cited

U.S. PATENT DOCUMENTS

| | | | |
|---|---|---|---|
| 2,800,616 | A | 7/1957 | Becker |
| 3,288,641 | A | 11/1966 | Rightmire |
| 3,727,616 | A | 4/1973 | Lenzkes |
| 4,134,408 | A | 1/1979 | Brownlee et al. |
| 4,441,498 | A | 4/1984 | Nordling |
| 4,561,443 | A | 12/1985 | Hogrefe et al. |
| 4,612,934 | A | 9/1986 | Borkan |
| 5,193,539 | A | 3/1993 | Schulman et al. |
| 5,193,540 | A | 3/1993 | Schulman et al. |
| 5,312,439 | A | 5/1994 | Loeb |

(Continued)

FOREIGN PATENT DOCUMENTS

| | | |
|---|---|---|
| WO | 97/18857 | 5/1997 |
| WO | 00/01320 | 1/2000 |

(Continued)

OTHER PUBLICATIONS

U.S. Appl. No. 60/748,240, filed Dec. 7, 2005, He et al.

(Continued)

*Primary Examiner* — Mark W Bockelman
(74) *Attorney, Agent, or Firm* — Wong, Cabello, Lutsch, Rutherford & Brucculeri, LLP.

(57) ABSTRACT

An exemplary system for communicating with an implantable stimulator includes a coil configured to transmit a signal modulated with either on-off keying (OOK) modulation or Frequency Shift Keying (FSK) modulation. The system further includes a first telemetry receiver in the implantable stimulator configured to receive the signal in accordance with the OOK modulation and a second telemetry receiver in the implantable stimulator configured to receive the signal in accordance with the FSK modulation.

25 Claims, 7 Drawing Sheets

(56) References Cited

U.S. PATENT DOCUMENTS

| | | | |
|---|---|---|---|
| 5,314,458 | A | 5/1994 | Najafi et al. |
| 5,372,605 | A | 12/1994 | Adams et al. |
| 5,405,367 | A | 4/1995 | Schulman et al. |
| 5,571,148 | A | 11/1996 | Loeb et al. |
| 5,642,030 | A | 6/1997 | Seelye |
| 5,750,926 | A | 5/1998 | Schulman et al. |
| 5,769,877 | A | 6/1998 | Barreras, Sr. |
| 5,807,397 | A | 9/1998 | Barreras |
| 5,861,019 | A | 1/1999 | Sun et al. |
| 5,951,594 | A | 9/1999 | Kerverm |
| 6,051,017 | A | 4/2000 | Loeb et al. |
| 6,061,596 | A | 5/2000 | Richmond et al. |
| 6,073,050 | A | 6/2000 | Griffith |
| 6,131,581 | A | 10/2000 | Leysieffer et al. |
| 6,148,235 | A | 11/2000 | Kuiper |
| 6,164,284 | A | 12/2000 | Schulman et al. |
| 6,175,764 | B1 | 1/2001 | Loeb et al. |
| 6,181,965 | B1 | 1/2001 | Loeb et al. |
| 6,185,452 | B1 | 2/2001 | Schulman et al. |
| 6,185,455 | B1 | 2/2001 | Loeb et al. |
| 6,195,585 | B1 | 2/2001 | Karunasiri et al. |
| 6,201,993 | B1 | 3/2001 | Kruse et al. |
| 6,208,894 | B1 | 3/2001 | Schulman et al. |
| 6,212,430 | B1 | 4/2001 | Kung |
| 6,214,032 | B1 | 4/2001 | Loeb et al. |
| 6,240,316 | B1 | 5/2001 | Richmond et al. |
| 6,259,937 | B1 | 7/2001 | Schulman et al. |
| 6,280,873 | B1 | 8/2001 | Tsukamoto |
| 6,315,721 | B2 | 11/2001 | Schulman et al. |
| 6,366,817 | B1 | 4/2002 | Kung |
| 6,400,991 | B1 | 6/2002 | Kung |
| 6,424,867 | B1 * | 7/2002 | Snell et al. .................. 607/31 |
| 6,434,194 | B1 * | 8/2002 | Eisenberg et al. ............ 375/238 |
| 6,443,891 | B1 * | 9/2002 | Grevious ................. 600/302 |
| 6,458,171 | B1 | 10/2002 | Tsukamoto |
| 6,516,227 | B1 | 2/2003 | Meadows et al. |
| 6,553,263 | B1 | 4/2003 | Meadows et al. |
| 6,567,703 | B1 | 5/2003 | Thompson et al. |
| 6,582,441 | B1 | 6/2003 | He et al. |
| 6,605,382 | B2 | 8/2003 | Ruth et al. |
| 6,607,843 | B2 | 8/2003 | Ruth, II et al. |
| 6,631,296 | B1 | 10/2003 | Parramon et al. |
| 6,826,430 | B2 | 11/2004 | Faltys et al. |
| 6,920,359 | B2 | 7/2005 | Meadows et al. |
| 6,978,181 | B1 * | 12/2005 | Snell .......................... 607/60 |
| 7,177,698 | B2 | 2/2007 | Klosterman et al. |
| 7,209,792 | B1 | 4/2007 | Parramon et al. |
| 7,822,480 | B2 * | 10/2010 | Park et al. .................. 607/60 |
| 2001/0053476 | A1 | 12/2001 | Ruth et al. |
| 2002/0055779 | A1 | 5/2002 | Andrews |
| 2003/0078634 | A1 | 4/2003 | Schulman |
| 2003/0171787 | A1 | 9/2003 | Money et al. |
| 2005/0021108 | A1 | 1/2005 | Klosterman et al. |
| 2007/0032839 | A1 | 2/2007 | Parramon et al. |

FOREIGN PATENT DOCUMENTS

| | | |
|---|---|---|
| WO | 01/60450 | 8/2001 |
| WO | 01/82398 | 11/2001 |
| WO | 02/09808 | 2/2002 |
| WO | 02/22205 | 3/2002 |
| WO | 03/005465 | 1/2003 |

OTHER PUBLICATIONS

Cameron, et al., "Micromodular Implants to Provide Electrical Stimulation of Paralyzed Muscles and Limbs," IEEE Transactions on Biomedical Engineering, vol. 44, No. 9, (Sep. 1997), pp. 781-790.

Loeb, et al., "North Sea: Transducers and Electrodes—Injectable Microstimulator for Functional Electrical Stimulation," Med. & Biol. Eng. & Computer, North Sea Special Feature, 29 (Nov. 1991), pp. NS13-NS19.

Loeb, et al., "BION™ Bionic Neurons for Functional and Therapeutic Electrical Stimulation," 20th Annual International Conference of IEEE Engineering in Medicine and Biology "Biomedical Engineering Towards the Year 2000 and Beyond," Oct. 29-Nov. 1, (1998), Hong Kong, 5 pages.

* cited by examiner

SYSTEMS AND METHODS FOR COMMUNICATING WITH AN IMPLANTABLE STIMULATOR

RELATED APPLICATIONS

The present application is a continuation of U.S. patent application Ser. No. 11/043,404, filed Jan. 25, 2005 now U.S. Pat No. 7,822,480, which was a continuation-in-part of U.S. patent application Ser. No. 10/607,962, filed Jun. 27, 2003, (now U.S. Pat. No. 7,177,698) which claims the benefit of Provisional Application Ser. No. 60/392,475, filed Jun. 28, 2002. Priority is claimed to all of these patent applications under 35 U.S.C. §120 or 119(e), and all are incorporated herein by reference in their entireties.

BACKGROUND

Radio-frequency (RF) powered implantable stimulators and battery powered implantable stimulators are described in the art. See, for instance, U.S. Pat. Nos. 5,193,539 ("Implantable Microstimulator); 5,193,540 ("Structure and Method of Manufacture of an Implantable Microstimulator"); 5,312,439 ("Implantable Device Having an Electrolytic Storage Electrode"); 6,185,452 ("Battery-Powered Patient Implantable Device"); 6,164,284 and 6,208,894 (both titled "System of Implantable Device for Monitoring and/or Affecting Body Parameters"). Each of these patents is incorporated herein by reference in its respective entirety.

Implantable stimulators configured to prevent or treat various disorders associated with prolonged inactivity, confinement or immobilization of one or more muscles are taught, e.g., in U.S. Pat. Nos. 6,061,596 ("Method for Conditioning Pelvis Musculature Using an Implanted Microstimulator"); 6,051,017 ("Implantable Microstimulator and Systems Employing the Same"); 6,175,764 ("Implantable Microstimulator System for Producing Repeatable Patterns of Electrical Stimulation"); 6,181,965 ("Implantable Microstimulator System for Prevention of Disorders"); 6,185,455 ("Methods of Reducing the Incidence of Medical Complications Using Implantable Microstimulators"); and 6,214,032 ("System for Implanting a Microstimulator"). Each of these patents is incorporated herein by reference in its respective entirety.

A typical implantable stimulator is intended to permanently remain in the body of a patient once it is implanted. Hence, transcutaneous communication between an implantable stimulator and an external device is important for the stimulator to function properly. For example, communication with the implantable stimulator may be effected to perform a number of functions including, but not limited to, transferring power to the stimulator, transferring data to and from the stimulator, programming the stimulator, and monitoring the stimulator's various functions.

SUMMARY

An exemplary system for communicating with an implantable stimulator includes a coil configured to transmit a signal modulated with on-off keying (OOK) modulation to transmit control data. The exemplary system further includes a first telemetry receiver in the implantable stimulator configured to receive the control data in accordance with the OOK modulation.

An exemplary method of communicating with an implantable stimulator includes modulating a signal with control data using on-off keying (OOK) modulation and transmitting the signal to the implantable stimulator.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

Throughout the drawings, identical reference numbers designate similar, but not necessarily identical, elements.

DETAILED DESCRIPTION

Several types of implantable stimulators and external devices utilize a magnetic field to achieve transcutaneous communication via a bidirectional telemetry link. An implantable stimulator and an external device typically both have an RF coil that is used as the transmitter and receiver of the magnetic field. Accurate communication between an implantable stimulator and an external device typically requires a precise reference clock within the implantable stimulator. The reference clock allows timing synchronization in the transmission of data to and from the implantable stimulator so that the implantable stimulator may demodulate data that has been modulated by the external device.

Many implantable stimulators include a precision circuit configured to provide the precise reference clock. The precision circuit may require calibration data for the reference clock to be synchronized with the frequency of the transmitting coil of the external device. This calibration data may be transmitted by the external device via the bidirectional telemetry link. However, in some instances, the bidirectional telemetry link may fail due to a number of factors including, but not limited to, a loss of battery power in the stimulator, interference, and/or coil malfunction. Without a functioning telemetry link between the external device and the implantable stimulator, important control data such as, but not limited to, the calibration data may not be transmitted to the implantable stimulator.

Hence, systems and methods for communicating with an implantable stimulator are described herein. A coil may be configured to transmit a signal including control data in accordance with a first telemetry scheme or a second telemetry scheme to an implantable stimulator. The implantable stimulator may include a first telemetry receiver for receiving the control data in accordance with the first telemetry scheme and a second telemetry receiver for receiving the control data in accordance with the second telemetry scheme. In some embodiments, the first telemetry scheme includes frequency shift keying (FSK) modulation and the second telemetry scheme includes on-off keying (OOK) modulation.

In the following description, for purposes of explanation, numerous specific details are set forth in order to provide a thorough understanding of the present system and method. It will be apparent, however, to one skilled in the art that the present system and method may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1:
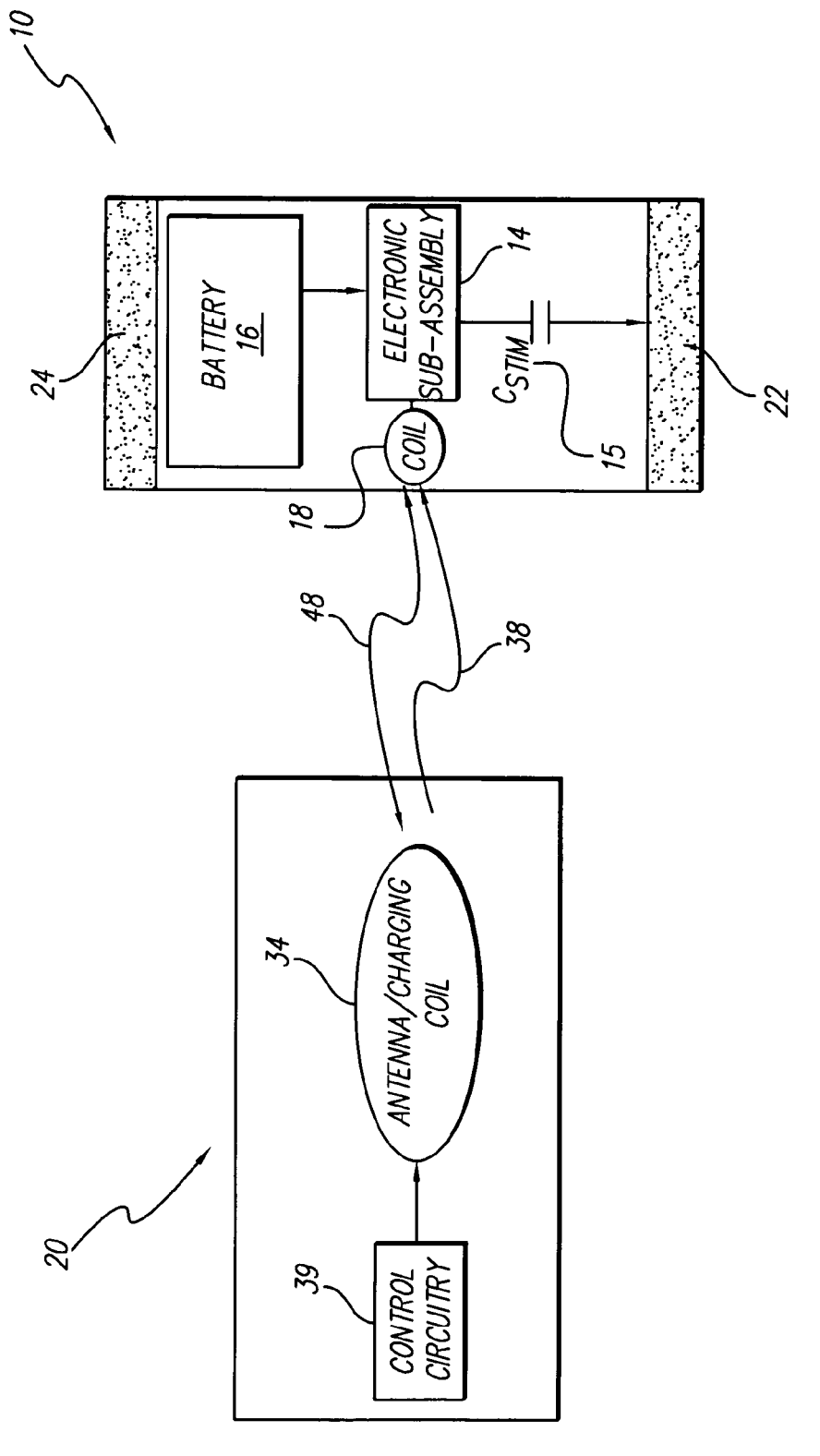
FIG. 1 shows an exemplary implantable stimulator and an exemplary external device according to principles described herein.

FIG. 1 shows an exemplary implantable stimulator (10) and an exemplary external device (20). The implantable stimulator (10) may be any type of implantable medical device, for example, an implantable microstimulator. Microstimulators are smaller than conventionally sized stimulators and are more easily implanted in a patient. Microstimulators may be injected through a large bore needle or placed via a small incision in the skin. An exemplary, but not exclusive, implantable microstimulator is the BION® microstimulator (Advanced Bionics® Corporation, Valencia, Calif.) which may be configured to stimulate tissue to alleviate urinary incontinence, reduce pain, or otherwise provide therapy for various disorders. Other examples of implantable stimulators include, but are not limited to, spinal cord stimulators (SCS), cochlear implants, and deep brain stimulators. As used herein and in the appended claims, unless otherwise specifically denoted, the terms "stimulator" and "microstimulator" will be used interchangeably to refer to any implantable medical device that may be implanted within a patient for therapeutic purposes. A typical stimulator or microstimulator is configured to transcutaneously communicate with an external device.

The implantable stimulator (10) may be implanted in the target tissue area of a patient and the external device (20) may be used to communicate with and/or transfer power to the stimulator (10). Such communication and/or power transfer may include, but is not limited to, transcutaneously transmitting data to the stimulator (10), receiving data from the stimulator (10), transferring power to a battery (16) in the stimulator (10), and/or providing recovery power to the battery (16) when the battery has been depleted to zero volts.

As illustrated in FIG. 1, the implantable stimulator (10) may include a number of components. A battery (16), which may be rechargeable, is configured to supply the stimulator (10) with power. A coil (18) is configured to receive and/or emit a magnetic field that is used to communicate with the external device (20). The coil (18) may also be used to receive energy used to recharge the battery (16). A stimulating capacitor (15) and two or more electrodes (22, 24) are configured to stimulate tissue with electric current. One or more of these components may be housed within a case (not shown). The stimulator (10) may include additional and/or different electronic sub-assembly (14) configured to perform a variety of functions as best serves a particular application.

The functions performed by the external device (20) will vary as best serves the particular application of the stimulator (10). The shape and design of the external device (20) will likewise vary. The external device (20) may be embodied by the external components (20) shown in FIG. 1 of the present application's parent application (U.S. patent application Ser. No. 10/607,962). For example, the external device (20) may include a chair pad and a base station. In use, the chair pad may be placed on a chair, and a patient who has an implanted stimulator (10) may sit on the chair pad to recharge the battery (16) in the stimulator (10) and/or to transfer data between the base station and the stimulator (10). The external device (20) may alternatively be a remote control or any other external component. In general, the external device (20) may be any device configured to communicate with and/or transfer power to an implantable stimulator (10).

The exemplary external device (20) of FIG. 1 may include control circuitry (39) and an antenna/charging coil (34) configured to emit and/or receive a magnetic field that is used to communicate with the implantable stimulator (10). The control circuitry (39) may be any circuitry configured to control the operation of the antenna/charging coil (34). In some examples, the antenna/charging coil (34) and the coil (18) of the stimulator (10) communicate by sending RF signals across a bidirectional telemetry link (48). The RF signals sent across the bidirectional telemetry link (48) may be modulated using a frequency dependent telemetry scheme, such as frequency shift keying (FSK), or by some other modulation scheme. The antenna/charging coil (34) and the coil (18) of the stimulator (10) may also communicate via a forward telemetry link (38). The forward telemetry link (38) may use an on/off keying (OOK) modulation scheme. The forward telemetry link (38) is also known as an OOK telemetry link. On/off keying (OOK) modulation is frequency independent and is also known as pulse width modulation (PWM). The forward telemetry link (38) will be described in more detail below.

The external device (20) may be configured to perform any number of functions via the bidirectional telemetry link (48) and/or the forward telemetry link (38). For example, the external device (20) may be configured to transcutaneously charge the rechargeable battery (16) in the implanted stimulator (10). The external device (20) may also be configured to transcutaneously transmit data to the stimulator (10), receive data from the stimulator (10), and/or provide recovery power to the rechargeable battery (16) when the battery (16) has been depleted to zero volts. The transmitted data may include configuration bits, programming bits, calibration bits, and/or other types of data.

Figure 2:
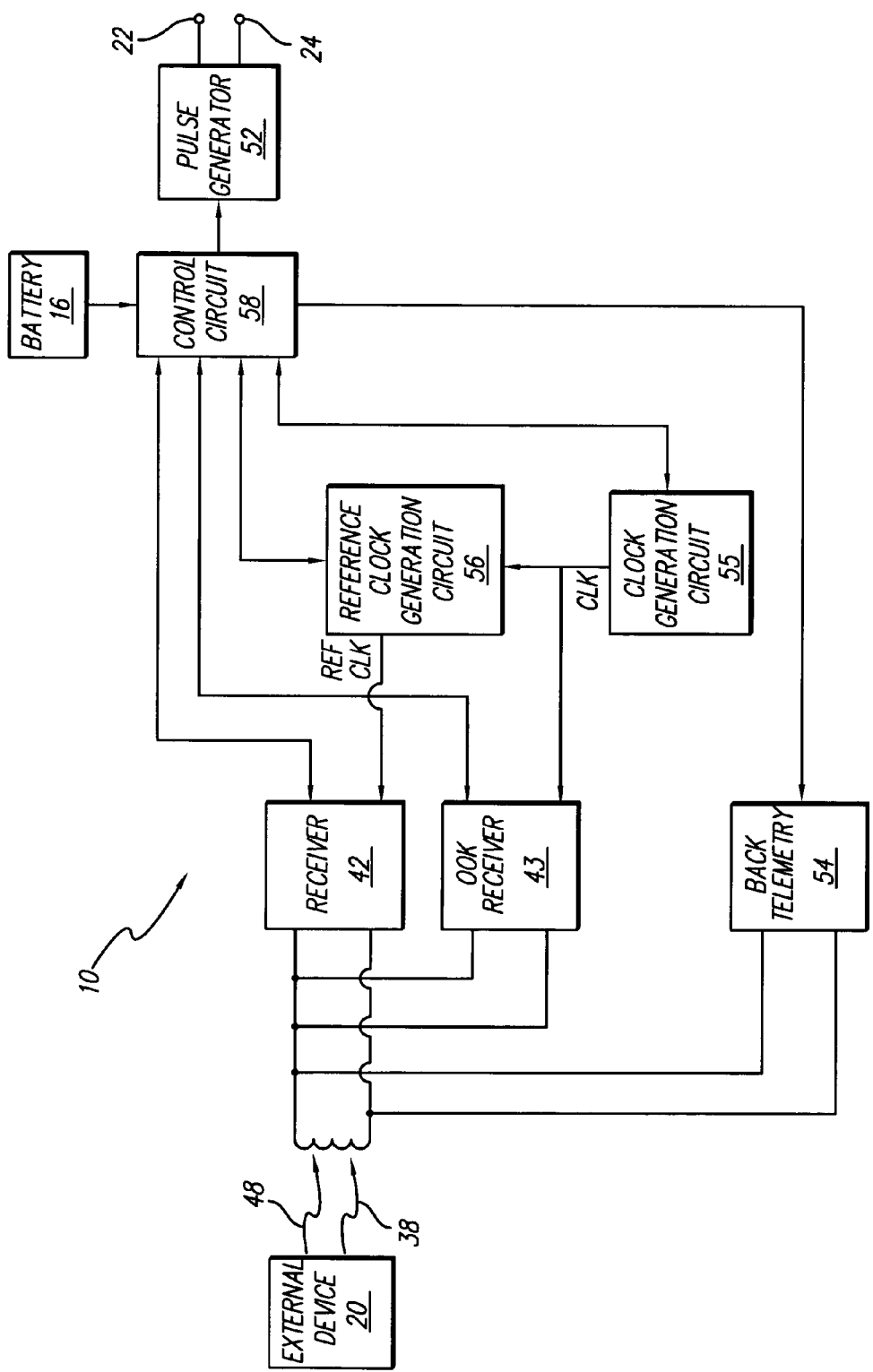
FIG. 2 shows a functional block diagram of an exemplary implantable stimulator according to principles described herein.

FIG. 2 shows a functional block diagram of an exemplary implantable stimulator (10). As shown in FIG. 2, the coil (18) may be coupled to a receiver (42) and configured to receive an RF signal via the bidirectional telemetry link (48). The receiver (42) may be any circuit configured to receive and process an RF signal. For example, the receiver (42) may be a microprocessor, digital signal processor (DSP), application specific integrated circuit (ASIC), processor with firmware, field programmable gate array (FPGA), or any other combination of hardware and/or software.

The RF signal may be sent by the external device (20), for example, and may include a carrier signal having modulated control data. The receiver (42) may then rectify the carrier signal to provide charging power for the rechargeable battery (16) and demodulate the carrier signal to extract the control data. As used herein and in the appended claims, the terms "control data" or "control bits" will be used to refer to any data or bits that are transmitted from the external device (20) to the implantable stimulator (10) or from the implantable stimulator (10) to the external device (20). For example, the control data may include, but is not limited to, calibration data used by a reference clock generation circuit (56) and programming data used by a control circuit (58).

As shown in FIG. 2, the control data may be input into the control circuit (58). The control circuit (58) is configured to control the operation of the stimulator (10). For example, the control circuit (58) may cause a pulse generator circuit (52) to generate and deliver electrical stimulation pulses to a patient through the electrodes (22, 24). The control circuit (58) may be a microprocessor, DSP, ASIC, processor with firmware, FPGA, or any other combination of hardware and/or software.

In some embodiments, the coil (18) may also be connected to a back telemetry circuit (54) to allow telemetry data to be sent from the stimulator (10) to the external device (20). The back telemetry circuit (54) may be any circuit configured to transmit data. The coil (18) may also be connected to an OOK receiver (43) to receive OOK modulated data. The OOK receiver (43) may be any circuit configured to receive and process an RF signal that has been OOK modulated. For example, the OOK receiver (43) may be a microprocessor, DSP, ASIC, processor with firmware, FPGA, or any other combination of hardware and/or software. Furthermore, the OOK receiver (43) may be integrated into the receiver (42). The function of the OOK receiver (43) will be described in more detail below.

Referring to FIG. 2, the receiver (42) may require a precise reference clock (ref clk) to rectify and/or demodulate the RF signal. The precise reference clock, as known in the art, may provide a clock signal having a frequency that is synchronized with the frequency used by the external device (20) to generate the RF signal. In some embodiments, the precise reference clock signal is generated by a reference clock generation circuit (56). As shown in FIG. 2, the reference clock generation circuit (56) generates the precise reference clock signal based on a clock signal generated by a clock generation circuit (55). The clock signal is also known as the system clock. The clock generation circuit (55) may be any clock generation circuit known in the art and may output a clock signal having an arbitrary frequency that remains constant over time. In the illustrated example, the reference clock generation circuit (56) includes precise resistor-capacitor (RC) networks and/or IC networks configured to process the clock signal output by the clock generation circuit (55) and generate the precise reference clock signal.

The reference clock generation circuit (56) and the clock generation circuit (55) are illustrated as separate components within the stimulator (10). However, it will be understood that the reference clock generation circuit (56) and/or the clock generation circuit (55) may be integrated into a single component, integrated into the control circuit (58), or integrated into any other circuitry included in the stimulator (10).

In some embodiments, the reference clock generation circuit (56) requires calibration data to synchronize the frequency of the reference clock signal with the frequency used by the external device (20) to generate the RF signal. This calibration data may be periodically sent, for example, from the external device (20) via the bidirectional telemetry link (48). However, if the bidirectional telemetry link (48) is disabled for any of a number of reasons, some of which will be described in detail below, the calibration data may not be conveyed to the reference clock generation circuit (56) resulting in a reference clock (ref clk) that is not synchronized with the frequency used by the external device (20). As will be described in more detail below, the frequency independent OOK telemetry link (38) may then be used to transmit the calibration data to the reference clock generation circuit (56).

The calibration data may then be used to resynchronize the reference clock (ref clk) with the frequency used by the external device (20) such that the bidirectional telemetry link (48) may again be used to transmit control data and/or transfer power from the external device (20) to the stimulator (10).

The implantable stimulator (10) of FIG. 2 may operate in a number of different states. For example, the stimulator (10) may operate in a normal operational state wherein the stimulator (10) receives RF signals from the external device (20) via the bidirectional telemetry link (48) and generates stimulation pulses. The stimulator (10) may enter into a hibernation state when the voltage output by the battery (16) falls below a voltage defined by a battery voltage hibernation level internal register (VHIB) (not shown). The VHIB is a programmable voltage value a of hibernation threshold for the battery (16). In the hibernation state, stimulation and FSK telemetry via the bidirectional telemetry link (48) are discontinued. However, in some embodiments, the stimulator (10) continues listening for an incoming OOK telemetry signal via the forward telemetry link (38). The stimulator (10) may also be configured to detect an applied external charging field used to charge the battery (16) while in the hibernation state.

The stimulator (10) may also operate in storage mode to conserve power. In storage mode, the stimulator (10) disables all circuitry except for circuitry that is used to recharge the battery (16) and circuitry used to listen for and receive an OOK telemetry signal via the forward telemetry link (38).

Hence, the OOK telemetry link (38) allows the external device (20) to communicate with the stimulator (10) even when the stimulator (10) is not actively listening for an RF signal to be transmitted via the bidirectional telemetry link (48), e.g., when the stimulator (10) is operating in the hibernation state or in the storage state. The OOK telemetry link (38) also provides a communication interface between the external device (20) and the stimulator (10) that may be used in emergency situations, e.g., when the bidirectional telemetry link (48) fails or when there is an emergency power shutdown.

Figure 3:
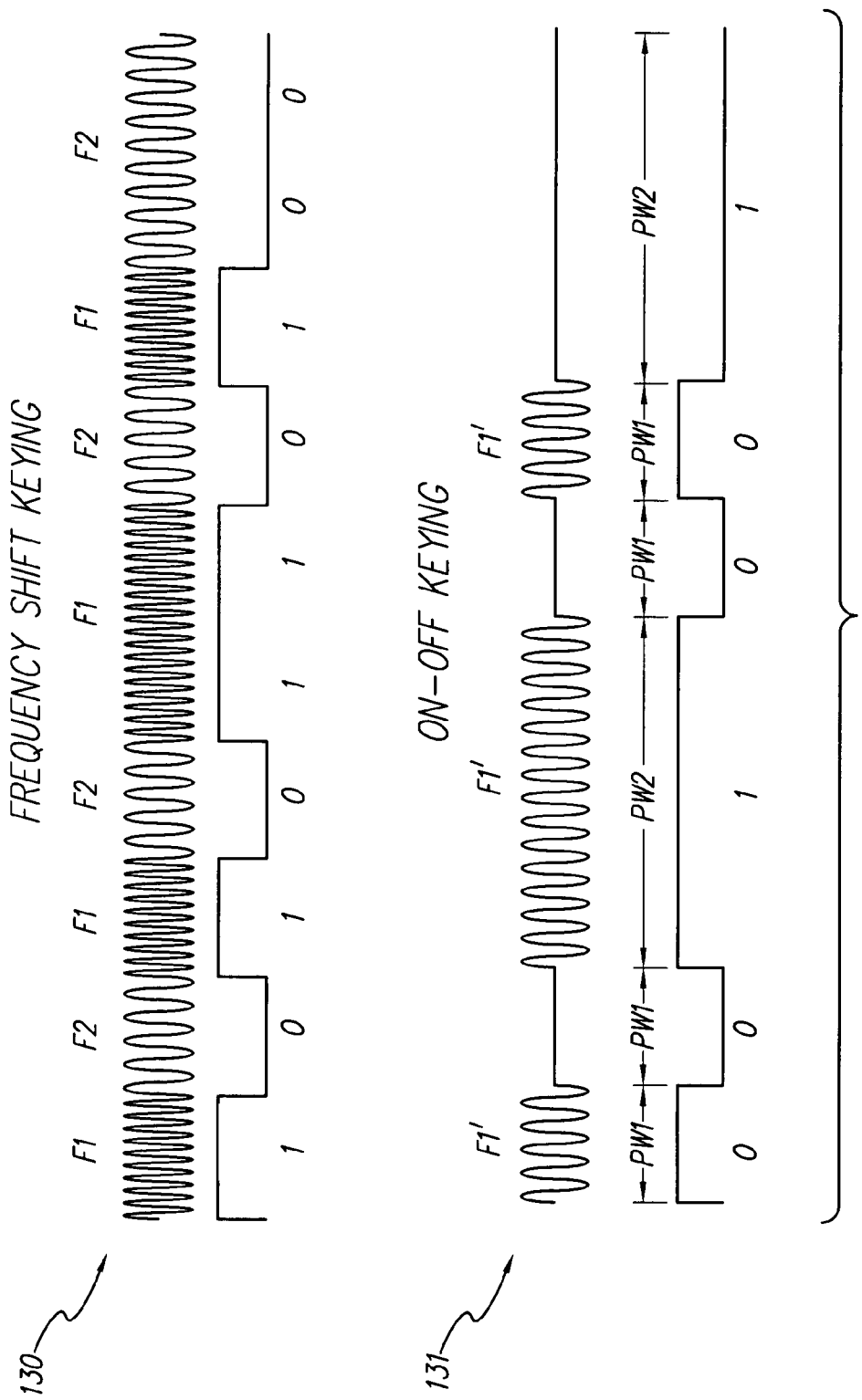
FIG. 3 shows a first signal including control data that has been modulated using frequency shift keying (FSK) and a second signal including control data that has been modulated using on-off keying (OOK) according to principles described herein.

FIG. 3 shows a first signal (130) including control data that has been modulated using FSK and a second signal (131) including control data that has been modulated using OOK, or PWM. The first signal (130) may be transmitted via the bidirectional telemetry link (48; FIG. 1) and the second signal (131) may be transmitted via the OOK telemetry link (38; FIG. 1). As shown in FIG. 3, the frequency of the first signal (130) varies between two frequencies, F1 and F2. FIG. 3 shows that a binary "1" is represented by the first frequency F1, and a binary "0" is represented by the second frequency F2. Alternatively, the first frequency F1 may represent "0" and the second frequency F2 may represent "1". The first signal (130), as shown in FIG. 3, transmits the bits "1010110100" for illustrative purposes.

The second signal (131) of FIG. 3 has been modulated using OOK modulation. As shown in FIG. 3, the signal (131) includes either a first frequency F1' or no transmitted signal (frequency equals zero) for one of two pulse widths, PW1 or PW2. A transmitted signal having a first pulse width, PW1, regardless of whether the frequency is F1' or zero (off), is interpreted as, e.g., a binary "0"; whereas a transmitted signal having a second pulse width, PW2, regardless of whether the frequency is F1' or zero (off), is interpreted as, e.g., a binary "1". Alternatively, a "1" may correspond to PW1 and a "0" may correspond to PW2. A change from the F1' frequency to the zero (off) frequency is used to indicate a data transition from one bit to the next bit in the data stream.

Thus, as illustrated in FIG. 3, the signal (131) first has a frequency F1' for a pulse width of PW1, indicating a binary "0". The signal (131) then transitions to being "off" (frequency equal zero) for a pulse width of PW1, indicating another binary "0". The signal then transitions to having a frequency equal to F1' for a pulse width of PW2, indicating a binary "1". The rest of the states of the signal (131) are shown in FIG. 3. Thus, the second signal (131), as shown in FIG. 3, transmits the bits "001001."

As mentioned, the OOK receiver (43) of FIG. 2 may be configured to receive and demodulate an OOK signal sent via the OOK telemetry link (38). In order for the OOK receiver (43) to distinguish between the first and second pulse widths (PW1 and PW2), a start bit having a fixed pulse width may be sent to the implantable stimulator (10) before any other control bits are sent. The start bit may be a "0" or a "1"; however, for illustrative purposes, the start bit is a "0" in the examples described herein. The OOK receiver (43) may be configured to use the clock generated by the clock generation circuit (55; FIG. 2) to increment a counter for the duration of the fixed pulse width to determine a "bit width threshold." As will be explained in more detail below, the OOK receiver (43) may then compare the pulse widths of each of the subsequent control bits in the OOK signal to the bit width threshold and determine the values of the control bits.

Because the OOK receiver (43) compares pulse widths, the frequency of the clock signal generated by the clock generation circuit (55) does not have to be synchronized with the frequency of the external device (20) in order for the OOK receiver (43) to function. Hence, the OOK telemetry link (38) is considered to be "frequency independent" and may be used to communicate with a number of implantable stimulators (10) each having different system clock frequencies.

Figure 4:
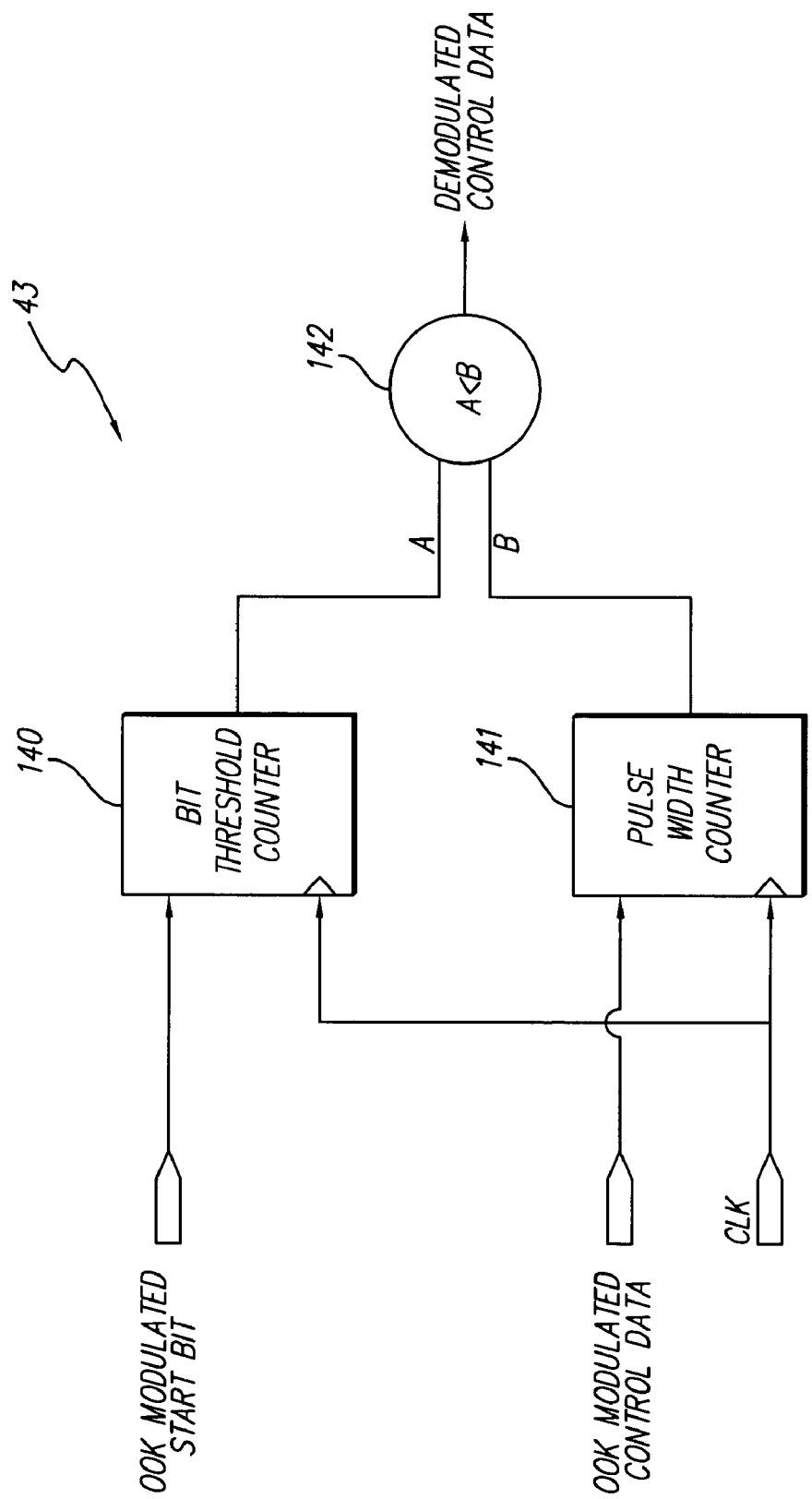
FIG. 4 illustrates an exemplary OOK receiver that may be used to receive and demodulate a stream of control bits that have been modulated using OOK modulation according to principles described herein.

FIG. 4 illustrates an exemplary OOK receiver (43) that may be used to receive and demodulate a stream of control bits that have been modulated using OOK modulation. As shown in FIG. 4, the OOK receiver (43) may include a bit threshold counter (140) configured to measure the pulse width corresponding to the start bit. The OOK receiver (43) may further include a pulse width counter (141) configured to measure the pulse widths of each of the control bits that are included in the OOK modulated control data subsequent to the start bit. The clock signal (clk) generated by the clock generation circuit (55; FIG. 2) is input into each of the counters (140, 141) to facilitate the counter functions. The counters (140, 141) may be any type of counter circuitry known in the art. For example, the counters (140, 141) may include flip-flop circuitry.

As shown in FIG. 4, the bit threshold counter (140) generates and outputs a value (A) representing the bit width threshold. The bit width threshold may be equal to the pulse width of the start bit or, alternatively, the bit width threshold may be a multiple of the actual number of samples taken by the bit threshold counter (140). For example, the bit threshold counter (140) may output a value that is two times the number of samples taken by the counter (140) such that the bit width threshold is equal to a higher value than the actual pulse width of the start bit.

The pulse width counter (141) also outputs a value (B) representing the pulse width for each control bit included in the modulated control data. A comparator (142) may then compare the pulse width of each of the control bits with the pulse width of the start bit. For illustrative purposes only, the start bit is a "0". Thus, if the pulse width of a particular control bit is greater than the pulse width of the start bit, the comparator (142) outputs a "1". Likewise, if the pulse width of a particular control bit is less than or equal to the pulse width of the control bit, the comparator (142) outputs a "0".

Figure 5:
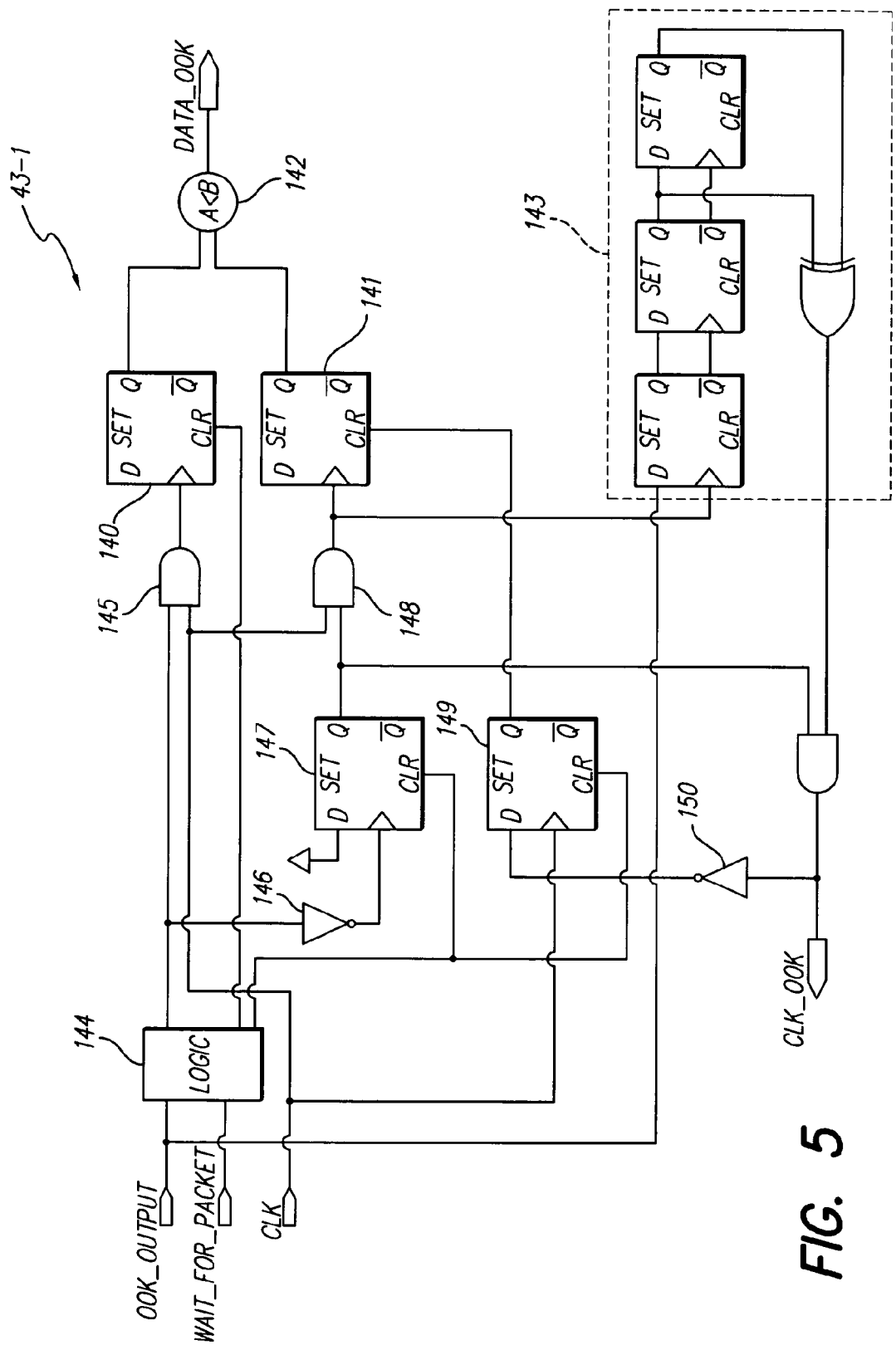
FIG. 5 illustrates an exemplary application specific integrated circuit (ASIC) implementation of an OOK receiver according to principles described herein.

FIG. 5 illustrates one exemplary implementation of the OOK receiver (43) of FIG. 4. The exemplary OOK receiver (43-1) illustrated in FIG. 5 is implemented using an ASIC. However, the OOK receiver (43), as described above, may be implemented using any of a variety of different combinations of hardware and/or software. FIG. 5 shows that the counters (140, 141) may be implemented using digital flip-flops. The flip-flops may be D flip-flops (140, 141), as shown in FIG. 5, or they may be any other type of flip-flop.

Figure 6:
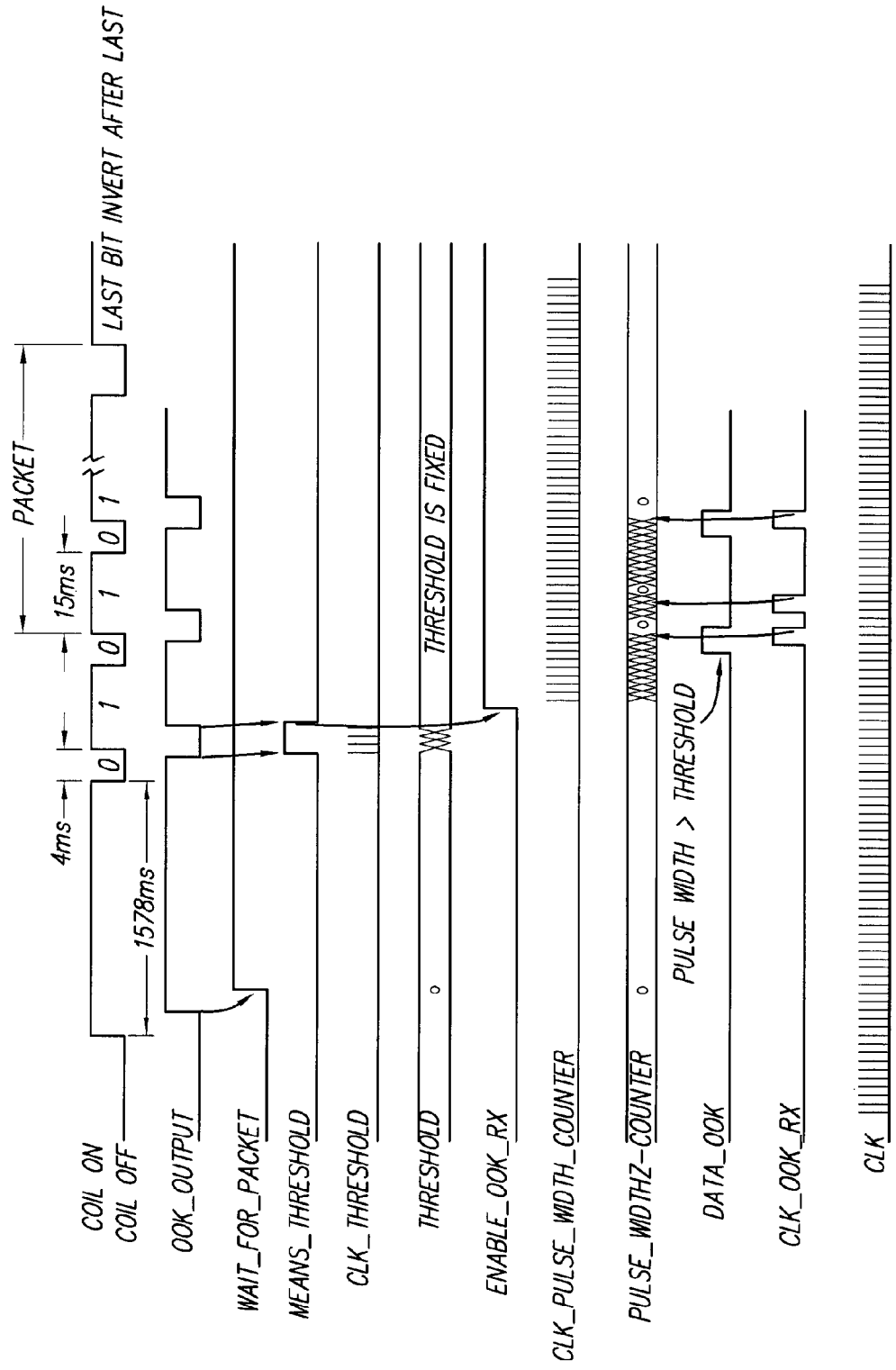
FIG. 6 is a timing diagram of various signals corresponding to the exemplary OOK receiver shown in FIG. 5 according to principles described herein.

As shown in FIG. 5, digital circuitry may be used in connection with the bit threshold counter (140), the pulse width counter (141), and the comparator (142). For example, logic (144) and AND gate (145) are used to cause the bit threshold counter (140) to only measure the pulse width of the start bit. Likewise, logic (144), inverters (146, 150), flip-flops (147, 149), and AND gate (148) are used to cause the pulse width counter (142) to measure the pulse widths of each of the subsequent control bits in the control data. The logic (144) may be any combination of digital logic as is known in the art. FIG. 5 also shows that the OOK receiver (43-1) may include an edge detector circuit (143) that may be used to generate a clock signal (clk_ook) for the demodulated control data (DATA_OOK). Exemplary VHDL (Very High Speed Integrated Circuit Hardware Description Language) code that may be used to program the OOK receiver (43-1) is shown in the Appendix that accompanied parent application Ser. No. 11/043,404, filed Jan. 25, 2005, which is incorporated by reference above. FIG. 6 is a timing diagram of various signals corresponding to the OOK receiver (43-1) shown in FIG. 5 and the VHDL code listed in the Appendix.

Figure 7:
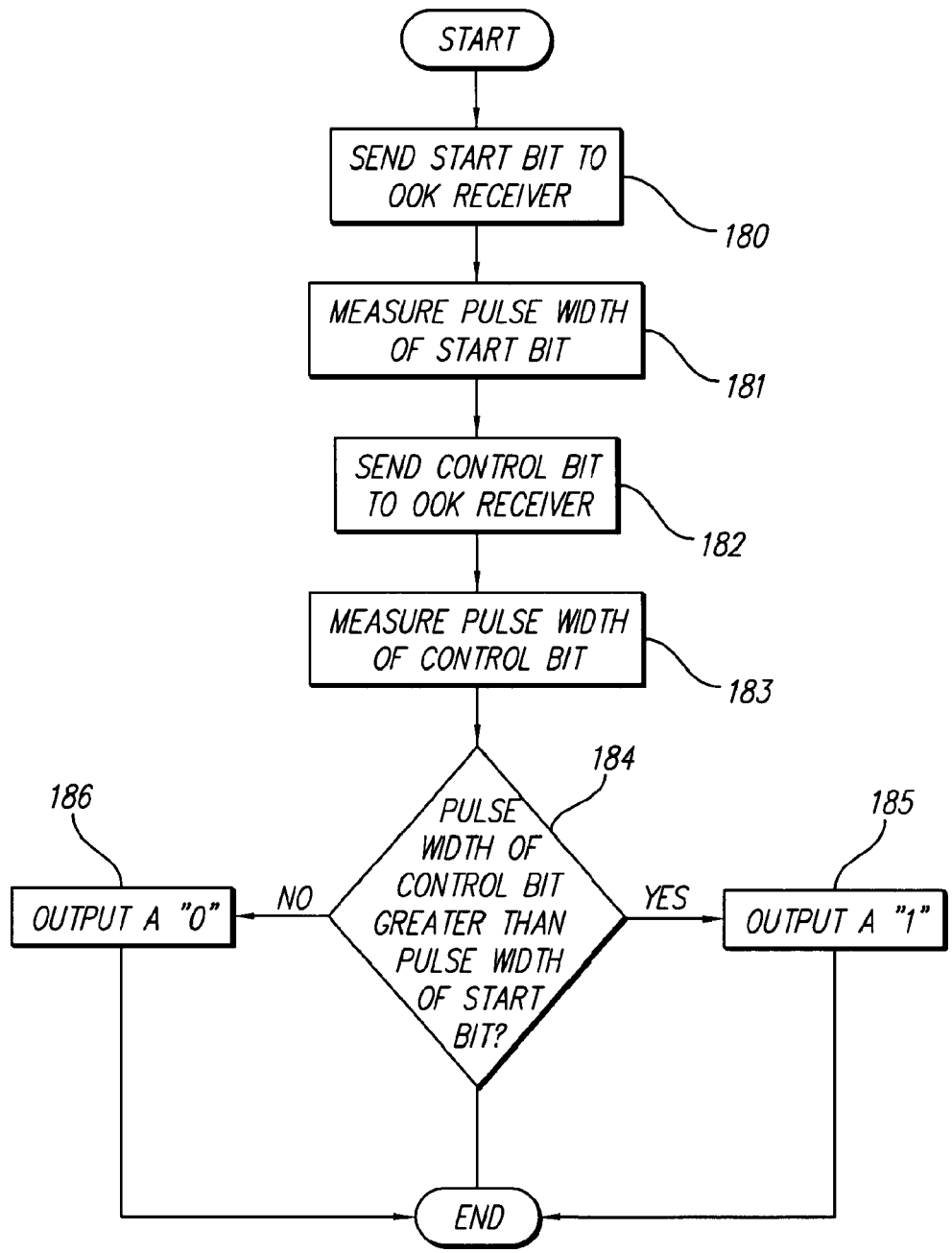
FIG. 7 is a flow chart illustrating an exemplary method of communicating with an implantable stimulator using OOK modulation according to principles described herein.

FIG. 7 is a flow chart illustrating an exemplary method of communicating with an implantable stimulator (10; FIG. 1) using OOK modulation. As shown in FIG. 7, a start bit is first sent to the OOK receiver (43; FIG. 4) (step 180). The pulse width of the start bit is then measured (step 181). A control bit may then be sent to the OOK receiver (43; FIG. 4) (step 182). The pulse width of the control bit is then measured (step 183). The pulse width of the control bit and the pulse width of the start bit are then compared (step 184). If the pulse width of the control bit is greater than the pulse width of the start bit (Yes; step 184), a control bit having a value of "1" may be output by the comparator (step 185). However, if the pulse width of the control bit is not greater than the pulse width of the start bit (No; step 184), a control bit having a value of "0" may be output by the comparator (step 186).

The preceding description has been presented only to illustrate and describe embodiments of invention. It is not intended to be exhaustive or to limit the invention to any precise form disclosed. Many modifications and variations are possible in light of the above teaching. It is intended that the scope of the invention be defined by the following claims.

What is claimed is:

1. A system, comprising:
   an external device, comprising
      control circuitry for producing from first data a first signal modulated with pulse width modulation, and for producing from second data a second signal modulated with frequency modulation; and
      a first antenna configured to wirelessly transmit the first modulated signal and the second modulated signal to the implantable medical device; and
   an implantable medical device, comprising:
      a first telemetry receiver in the implantable medical device for demodulating the first modulated signal to recover the first data; and
      a second telemetry receiver in the implantable medical device for demodulating the second modulated signal to recover the second data.

2. The system of claim 1, wherein the pulse width modulation comprises on-off keying (OOK) modulation.

3. The system of claim 1, wherein the frequency modulation comprises frequency shift keying (FSK) modulation.

4. The system of claim 1, wherein the implantable medical device further comprises a reference clock generation circuit for generating a reference clock signal used by the second telemetry receiver.

5. The system of claim 4, wherein the first data comprises calibration data used to calibrate the reference clock generation circuit such that the reference clock signal is synchronized with a frequency used to transmit the second modulated signal.

6. The system of claim 1, wherein the first data comprises a start bit and a number of control bits, the start bit being transmitted before the control bits.

7. The system of claim 6, wherein the first telemetry receiver comprises:
 a bit threshold counter configured to measure a pulse width of the start bit to generate a bit width threshold;
 a pulse width counter configured to measure a pulse width of the bits; and
 a comparator configured to compare the measured pulse widths with the bit width threshold to determine whether a bit comprises a logic '0' or a logic '1'.

8. The system of claim 1, wherein the implantable medical device comprises at least one electrode for stimulating a patient's tissue.

9. The system of claim 1, wherein the first data enables the second telemetry receiver to receive the second modulated signal.

10. The system of claim 1, wherein the first and second telemetry receivers are coupled to a second antenna.

11. The system of claim 1, wherein the first signal is used to communicate with the implantable medical device while in the low power state.

12. A system, comprising:
 an external device comprising a first coil coupled to control circuitry configured to transmit data in accordance with a first telemetry scheme and a second telemetry scheme; and
 an implantable medical device, comprising:
  a second coil, and
  telemetry circuitry coupled to the second coil for listening for and recovering the transmitted data whether transmitted in accordance with the first telemetry scheme or the second telemetry scheme, wherein the telemetry circuitry discontinues listening for the data transmitted in accordance with the first telemetry scheme when the implantable medical device while in a low power state, and wherein the telemetry circuitry continues listening for the data transmitted in accordance with the second telemetry scheme when the implantable medical device is in the power state.

13. The system of claim 12, wherein the first telemetry scheme comprises a frequency shift key telemetry scheme wherein a binary '1' is represented by a transmitted signal of a first frequency, and wherein a binary '0' is represented by a transmitted signal of a second frequency.

14. The system of claim 12, wherein the second telemetry scheme comprises an On-Off-Keying (OOK) Pulse Width Modulation (PWM) telemetry scheme wherein a binary '0' is represented by a first pulse width and a binary '1' is represented by a second pulse width.

15. The system of claim 14, wherein a transition between one data bit and an adjacent data bit is marked by a change in a transmitted data signal from an ON to an OFF state or from an OFF to an ON state, wherein the ON state is characterized by the presence of a data signal having a frequency, and wherein the OFF state is characterized by the absence of the data signal.

16. The system of claim 12, wherein the telemetry circuitry is bidirectional for allowing data to be sent to and received from the external device.

17. The system of claim 12, wherein the first telemetry scheme employs radio frequency (RF) telemetry, and wherein the second telemetry scheme employs inductive telemetry.

18. The system of claim 17, wherein the first telemetry scheme comprises a frequency shift key (FSK) communication scheme, and the second telemetry scheme comprises an On-Off-Keying (OOK) Pulse Width Modulation (PWM) communication scheme.

19. The system of claim 12, wherein the implantable medical device further comprises at least one electrode for stimulating the tissue of a patient.

20. The system of claim 12, wherein the telemetry circuitry comprises first telemetry circuitry for recovering the transmitted data when transmitted in accordance with the first telemetry scheme and second telemetry circuitry for recovering the transmitted data when transmitted in accordance with the second telemetry scheme.

21. The system of claim 12, wherein the data comprises a start bit and a number of control bits.

22. The system of claim 12, wherein the second telemetry scheme is frequency independent.

23. The system of claim 12, wherein the low power state comprises one or more of (i) a hibernation state, (ii) a storage state, and (iii) an emergency power shutdown.

24. The system of claim 23, wherein the implantable medical device comprises a battery, and wherein the hibernation state comprises a state when a voltage of the battery falls below a threshold.

25. The system of claim 23, wherein the implantable medical device comprises a battery, and wherein the storage state comprises a state in which all circuitry in the implantable medical device is disabled except for circuitry used to recharge the battery and the telemetry circuitry which continues listening for the data transmitted in accordance with the second telemetry scheme.

* * * * *